United States Patent [19]

Nojiri et al.

[11] Patent Number: 4,939,114

[45] Date of Patent: Jul. 3, 1990

[54] SILVER-DEPOSITED CATALYST FOR PRODUCTION OF ETHYLENE OXIDE

[75] Inventors: Naohiro Nojiri; Yukio Sakai; Yoshiaki Saotome; Tomoatsu Iwakura, all of Ami, Japan

[73] Assignee: Mitsubishi Petrochemical Co., Ltd., Tokyo, Japan

[21] Appl. No.: 268,546

[22] Filed: Nov. 7, 1988

[51] Int. Cl.$^5$ .................. B01J 21/04; B01J 23/04; B01J 23/50

[52] U.S. Cl. .................................................. 502/348

[58] Field of Search ............................... 502/347, 348

[56] References Cited

U.S. PATENT DOCUMENTS

| | | | |
|---|---|---|---|
| 4,207,210 | 6/1980 | Kilty | 502/348 |
| 4,471,071 | 9/1984 | Rebsdat et al. | 502/348 |
| 4,728,634 | 3/1988 | Boxhoorn et al. | 502/348 X |

*Primary Examiner*—W. J. Shine
*Attorney, Agent, or Firm*—Wenderoth, Lind & Ponack

[57] ABSTRACT

A silver-deposited catalyst for the production of ethylene oxide by the oxidation of ethylene, said catalyst comprising (1) a carrier composed mainly of alpha-alumina, which carrier does not show acidity in a visual color change method in a toluene solvent using a dimethyl yellow indicator having a pKa of +3.3, and does not show basicity in a color reaction in a toluene solvent using a bromothymol blue having a pKa of +7.1, and (2) as catalyst components, silver and at least one cationic component selected from sodium, potassium, rubidium and cesium.

3 Claims, No Drawings

SILVER-DEPOSITED CATALYST FOR PRODUCTION OF ETHYLENE OXIDE

This invention relates to a silver-deposited catalyst for the production of ethylene oxide by the vapor-phase oxidation of ethylene.

Ethylene oxide is produced in quantities of the order of several million tons yearly throughout the world. To produce ethylene oxide efficiently, there has been a strong demand for improvement of catalysts, and it has been desired to develop a catalyst having high selectivity and a long lifetime.

Various methods have been proposed to achieve this desire. They are mainly directed firstly to the combination of silver as a main active component with additives such as alkalies and the optimization of the ratio between silver and the additives and secondly to the improvement of carriers for supporting these catalytic components. The latter intends to better the dispersion of silver by increasing the specific surface area of the carrier and permit use at low temperatures and enable the catalyst to be used for a long period of time with high selectivity. By simply increasing the surface area of the carrier, the intended effect cannot be obtained because there is an influence of diffusion and side-reactions may occur on the surface of the carrier. Further contrivance is therefore required. For example, Japanese Laid-Open Patent Publication No. 89843/1981 states that an alpha-alumina carrier having a low Na content of not more than 0.07% by weight is selected, and by combining it with 5–25% by weight of silver and 0.001 to 0.05 gram-equivalent of at least one alkali metal selected from potassium, rubidium and cesium, a surface area of 0.5 to 5 $m^2/g$ can be used.

Extensive investigations of the present inventors on practical catalysts mainly containing carriers of a higher surface area have shown that to produce a high-performance catalyst, the balance between the surface acidity and the surface basicity of the carrier is of essential importance, and that the presence of strong acid sites or basic sites on the surface of the carrier adversely affects the performance of the catalyst. To control the surface properties of the carrier, it is insufficient to adjust only the content of one component such as Na in the carrier, but it is necessary to adjust both of the acidic component and the basic component in the carrier.

It has been found that the acidity and basicity of the catalyst components supported on the carrier are also important, and by combining a carrier having controlled surface acidity and basicity with specific cationic components as catalyst components, a catalyst having high selectivity and a long life can be obtained.

Thus, the present invention provides a silver-deposited catalyst for the production of ethylene oxide by the oxidation of ethylene, said catalyst comprising (1) a carrier composed mainly of alpha-alumina, which carrier does not show acidity in a visual color change method in a toluene solvent using a dimethyl yellow indicator having a pKa of +3.3, and does not show basicity in a visual color change method in a toluene solvent using a bromothymol blue having a pKa of +7.1, and (2) as catalyst components, silver and at least one cationic component selected from sodium, potassium, rubidium and cesium.

The acidic and basic properties of the surface of the carrier can be easily determined by a visual color change in accordance with an indicator method (the visual color change method and the method of amine titration are described at page 5 et seq. of Kozo Tabe, "Solid Acids and Bases" published in 1970 by Academic Press Co. and page 170 et seq. of Catalyst Experimment Handbook, a separate voluem of Catalyst Lectures, edited by Catalysis Society of Japan, published on May 1, 1986 by Kodansha; the latter is a Japanese-language publication). When a weak acidic site exists on the surface of the carrier, the addition of an indicator which adsorbs on the weak site of the carrier sample in toluene (such as methyl red when pKa is +4.8) results in rapid adsorption of the indicator on the surface of the carrier and consequent development of an acidic color. To examine a strong acidic site, an indicator which adsorbs on the strong acidic site but not on a weak one (for example, dimethyl yellow with a pHa of +3.3) may be used. Accordingly, the use of indicators having different strengths gives information on the acid strength of the surface of the carrier. The amount of the acidic sites can be determined by titrating the sample subjected to a visual color change reaction with the indicator with a base such as n-butylamine. The color formation by the indicator and the end point of titration with the base can usually be determined fully by visual observation. If the determination is difficult, the accuracy of determination can be increased by back-titrating the supernatant left after the measurement, or by using a spectrophotometric method. The surface basicity, like surface acidity, can be determined by an indicator method. For example, when pKa is +7.1, bromothymol blue is used in a toluene solvent. If the carrier has surface basicity, the indicator adsorbs on the basic sites on the surface of the carrier to produce a blue basic color.

The carrier composed mainly of alpha-alumina used in this invention does not show acidity in a visual color change reaction in a toluene solvent using a dimethyl yellow indicator having a pKa of +3.3, and does not show basicity in a color reaction in a toluene solvent using a bromothymol blue having a pKa of +7.1. Preferably, measurement of the amount of acid with n-butylamine using methyl red having a pKa of +4.8 as an indicator gives a titration value of 0 to 2 micromoles/g. In other words, the carrier used in this invention is characterized by the fact that it does not have strong surface acidity which forms a color with an indicator having pKa of +3.3 and surface basicity which forms a color with an indicator having a pKa of +7.1. Preferably, it has weak surface acidity which forms a color with an indicator having a pKa of +4.8 and is represetned by a titration value of not more than 2 micromoles/g.

The present inventors already discovered that in a carrier composed mainly of alpha-alumina for use in a catalyst used to produce ethylene oxide, the silica content and the sodium content of the carrier are important. Further investigations have shown that the surface properties of the catalyst can be rendered further suitable not only by adjusting both the acidic component and the basic component, but also by controlling the balance between the two components.

The surface properties of the carrier are controlled particularly by the balance between the acidic component and the basic component on the surface of the carrier. Usually, the acidic component contained in a carrier composed mainly of alpha-alumina is silica. The surface acidity is regulated by the silica content of the carrier, particularly per unit surface area of the carrier.

The silica content is 0.3 to 20% by weight, preferably 0.5 to 10% by weight. Per unit surface area of the carrier, the silica content of the carrier is 0.1 to 40% by weight/m$^2$, preferably 0.15 to 30% by weight/m$^2$.

On the other hand, the surface basicity is usually regulated by an alkali component contained in the carrier, such as sodium and potassium. Where the alkali metal contained in the carrier is substantially limited to sodium, the sodium content in the carrier is 0.05 to 1% by weight, preferably 0.05 to 0.7% by weight. The weight ratio of silica to sodium (SiO$_2$/Na) is also important in controling the surface properties. If this ratio is within the range of 3 to 40, preferably 5 to 30, the balance between the acidic component and the basic component on the surface of the carrier is maintained, and the surface of the carrier can be maintained neutral to weakly acidic without rendering it strongly acidic and basic.

By regulating the acidic component and the basic component in the carrier, particularly its surface, it has become possible to use a carrier of a higher surface area. When the surface area of the carrier is rendered high, silver can be easily deposited on the carrier as fine particles. This leads to an increase in catalytic activity and in selectivity. Preferably, the carrier used in this invention has a surface area of 0.5 to 5 m$^2$/g, particularly 0.7 to 3 m$^2$/g, an average pore diameter of 0.5 to 3.5 microns, particularly 0.9 to 3.5 microns, and a water absorption of 20 to 50%, particularly 25 to 45%.

In addition to the surface properties of the carrier, a cationic component such as an alkali as a catalyst component is important in order to obtain high performance. The reason for this is not necessarily clear. It is presumed however that a catalyst having high selectivity and a long lifetime can be obtained by the synergestic effect of (1) the surface properties of a neutral to weakly acidic carrier containing neither a strong acidic site nor a strong basic cite resulting from controlling the ratio between the acidic comonent and the basic component in the alpha-alumina carrier, and (2) the controlling of these surface properties by adding a cationic component such as an alkali.

Accordingly, if the acidity and basicity of the carrier are beyond the power of controlling by a cationic component such as an alkali, high catalytic performance cannot be obtained. In other words, if a basic carrier is used, there results a catalyst having a lower initial performance and a shorter life time than in the case of using the carrier of this invention. Furthermore, if a carrier more acidic than the carrier used in this invention is used, the degradation of the initial performance can be suppressed to some extent by controlling the amount of the alkali component added. However, the performance of the catalyst are markedly changed with time, and its active lifetime is shorter than the catalyst of this invention.

The contents of silica and sodium in the carrier not only greatly affect the properties of the catalyst, but also are important for the strength of the carrier. Practical strength is difficult to obtain if the amount of sodium in the carrier is not more than 0.05% or the silica/sodium weight ratio (SiO$_2$/Na) is at least 40. Preferably, the carrier has a crush strength of at least 3 kg.

The catalyst of this invention can be produced by any conventional method. Preferably, it is prepared by a method which comprises impregnating the carrier with an aqueous solution, or a water-containing organic solvent solution, containing a silver salt and an amine as a complex-forming agent, heating the impregnated carrier, and preferably contacting it with a superheated steam at 130° to 300° C. to deposit silver on the carrier. The alkali component may be supported in advance on the carrier, or added to the silver solution, or added after the deposition of silver on the carrier.

The embodimnts of the present invention will be described.

Any silver compound which forms a complex soluble in an aqueous solvent with an amine, and decomposes at not more than 500° C., preferably not more than 300° C., more preferably not more than 260° C., to deposit silver may be used in this invention to form a silver as a catalyst component of the catalyst of this invention. Examples are silver oxide, silver nitrate, silver carbonate and silver salts of carboxylic acids such as silver acetate and silver oxalate. Silver oxalate is preferred. The amine as a complex-forming agent may be any amine compound which can solubilize the above silver compound in an aqueous solvent. Examples include pyridine, acetonitrile, ammonia and amines having 1 to 6 carbon atoms. Preferred are ammonia, pyridine, monoamines such as butylamine, alkanolamines such as ethanolamine, alkylenediamines having 2 to 4 carbon atoms, and polyamines. Ethylene diamine, 1,3-propanediamine, or particularly a mixture of these is preferred. It is practical to use an aqueous solution of the silver compound and the amine for impregnation in the carrier. A water-containing organic solvent solution, for example an aqueous alcohol solution, of these compounds may also be used. The concentration of silver in the impregnating solution is selected so that finally, 5 to 25% by weight of silver is deposited as a catalyst component. The impregnating operation is performed by an ordinary method. If required, pressure reduction, heating and spraying are carried out at the same time. The amine is added in an amount required to complex the silver compound (usually two amine groups correspond to one silver atom). Usually, it is safe to add it in an amount 5 to 30% in excess of the equivalent amount. The treatment after the impregnation is carried out by selecting the temperature and time required to deposit silver on the carrier. It is most desirable to select such conditions that silver exists on the carrier as fine particles as uniformly as possible. Generally, high temperatures and long periods of time are undesirable because they accelerate aggregation of the deposited silver particles. Preferably, therefore, the impregnated carrier is heat-treated for a short time of 5 minutes to 30 minutes by using air (or an inert gas such as nitrogen) heated to 130° to 300° C., or a superheated steam. The heat-treatment for a short period of time is preferred from the standpoint of shortening the time required for catalyst preparation. The use of superheated steam is preferred because the distribution of silver on the carrier becomes uniform.

Preferably, the cationic component constituting the catalyst is added in the form of a compound soluble in an aqueous solvent in a soluble concentration. It may partly be insoluble. Examples of such a compound are inorgnaic salts such as nitrates, carbonates, bicarbonates, halides, hydroxides, nitrites and sulfates and carboxylic acid salt such as formates. Preferably, a halogen salt such as a chlorine, bromine or fluorine salt is added as a catalyst compoennt in an amount of at least 5 ppm but not more than 0.1% by weight, preferably 7 ppm to 0.07% by weight. The cationic component may be added to the silver impregnating solution. Or it may be impreganted before or after the impregnation. The addition of sodium after the impregnation is inadequate. The impreganting solution is preferably an aqueous solution. The use of a solution containing an alcohol, etc. is not so desirable from the viewpoint of safety and simplification of the process.

The content of sodium as a catalyst component is preferably 50 ppm to 1% by weight in the catalyst. Advantageously, it is generally suitably 500 to 4000 ppm. Preferably, sodium is applied in the form of sodium carbonate or sodium bicarbonate. The content of at least one alkali component selected from potassium, rubidium and cesium in the catalyst is 10 to 2,000 ppm, preferably 20 to 2,500 ppm. The potassium content is 50 to 650 ppm, preferably 75 to 400 ppm. The rubidium content is 80 to 1300 ppm, preferably 100 to 1000 ppm. The cesium content is 150 to 2,000 ppm, preferably 200 to 1500 ppm. The addition of the alkali component is preferably effected simultaneously with silver. Preferably, the alkali component is added partly or wholly as a halide such as a chloride, bromide or fluoride, particularly the chloride. Preferably, barium is added in an amount of 30 to 1000 ppm, preferably 40 to 650 ppm. to the catalyst. It is suitably added in the form of a nitrate or hydroxide.

When the cationic component is added by impregnation other than simultaneous impregnation, it is preferred to deposit it on the carrier by drying the impregnated carrier for 5 minutes to 30 minutes using a superheated steam at 110° to 200° C. As a result, the cationic component is uniformly dispersed on the carrier. The carrier is preferably in the form of a sphere, a pellet or a ring with a size of about 3 to 10 mm. The main component of the carrrier is alpha-alumina, and its surface area is preferably 0.5 to 5 $m^2/g$, preferably 0.7 to 3 $m^2/g$. To retain strength and this surface area and facilitate the impregnation operation, the carrier advantageously has a water absorption of 20 to 50% preferably 25 to 45%. Pores having a size of not more than 0.1 micron are not desirable for the formation of ethylene oxide, and average pore diameters of less than 0.5 micron do not produce good results. If the average pore diameter is too large, the desired surface area cannot be attained. Accordingly, the preferred average pore diameter of the carrier used in this invention is 0.5 to 3.5 microns, preferably 0.9 to 3.5 microns.

The reaction of converting ethylene into ethylene oxide using the catalsyt of this invention can be performed by a conventional operating procedure. For example, the reaction pressure is 1 to 35 $kg/cm^2$-G, and the reaction temperature is 180° to 300° C., preferably 200° to 260° C. The concentration of ethylene is 1 to 40% by volume and the concentration of oxygen is 1 to 20% by volume. Generally, it is preferred to have a diluent such as methane present in the reaction gas in a concentration of 0 to 70% by volume. Oxygen may be fed in the form of air, or industrial oxygen. By adding a reaction modifier such as ethylene dichloride, the formation of hot spots in the catalyst can be prevented, and the performance, particularly the selectivity, of the catalyst are greatly improved. The amount of the reaction modifier is preferably several ppm to several tens of ppm.

The following Examples and Comparative Examples illustrate the present invention. In the tables, T40 and S40 represent the reaction temperature (°C., bath temperature) and the selectivity (%) of ethylene oxide based on ethylene when the proportion of oxygen converted was 40%.

EXAMPLE 1

An alpha-alumina carrier (8 mm in diameter, 3 mm in inner diameter, and 8 mm in length; ring-like, surface area 1.16 $m^2/g$, pore volume 0.38 ml/g, average pore diameter 1.5 microns, water absorption 38%) containing 0.5% of silica and 0.1% of sodium (weight of silica per unit surface area 0.43% by weight/$m^2$) was used, and a catalyst was prepared by the following procedure.

Sodium bicarbonate (13.2 g) was dissolved in 1 liter of water, and one kilogram of the carrier was immersed in the solution. The excess of the liquid was removed by allowing it to trickle down, and the carrier was dried with superheated steam at 150° C. for 15 minutes. Separately, 228 g of silver nitrate and 135 g of potassium oxalate ($K_2CO_4.H_2O$) were each dissolved in 1 liter of water and mixed, and the mixture was heated to 60° C. in a water bath to give a white precipitate of silver oxalate. After filtration, the precipitate was washed with distilled water to remove potassium from the precipitate. Separately, 200 ml of an aqueous solution containing 19.8 g of 1,3-propanediamine and 72.2 g of ethyenediamine in water was prepared. Under cooling with ice, the silver oxalate precipitate was added little by little to prepare a silver oxalate solution. The solution was mixed with 40 ml of an aqueous solution containing 0.065 g of barium hydroxide and 0.720 g of cesium chloride. Water was added to adjust the amount of the mixture to 342 ml, and the mixture was transferred to a rotary evaporator. The carrier described above which was dried after impregnation of sodium biccarbonate was put in the evaporator to performm an impregnation operation at 50° C. under rotation. In the initial stage of the impregnating operation, the pressure was reduced (100 mmHg), then returned to atmospheric pressure, and 5 minutes later, the carrier was taken out. the impregnated carrier was heated with superheated steam at 200° C. at a flow rate of 2 m/sec for 10 minutes to prepare the catalyst of this invention. The amounts of Ag, Na, Ba, Cs and Cl deposited were 12%, 0.2%, 50 ppm, 473 ppm and 126 ppm, respectively.

The catalyst prepared by the above method was crushed to a size of 6 to 10 mesh, and 3 ml of the crushed catalyst was filled in a steel reaction tube having an inside diameter of 7.5 mm. A reaction gas (composed of 30% by volume of ethylene, 8% by volume of oxygen, 1.5 ppm of vinyl chloride, 6% by volume of $CO_2$ and the remainder being nitrogen) was passed through the reaction tube under a pressure of 18 $kg/cm^2$-G at an SV of 4000/h. After the lapse of one week when the oxygen conversion was 40%, the reaction temperature (T40) was 222° C., and the selectivity of ethylene oxide based on ethylene (S40) was 80.1%.

The carrier used in Example 1 had a crush strength, measured by using a Kiya-type hardness tester (1600-D) and averaging the measured strengths of 50 carrier particles, of 5.2 kg. This strength was satisfactory for practical purposes.

The carrier was subjected to the following visual color change reactions. Twenty grams of the carrier was pulverized in an agate mortar, and fragments finer than 100 mesh were dried at 120° C. for 3 hours. Twenty milliliters of dry toluene was put in a 100 ml flask with a ground stopper. Five grams of the carrier sample which was allowed to cool in the desiccator after drying was put in the flask. Five milliliters of a solution of 0.001% of an indicator in toluene was added.

The solution was well shaken and then allowed to stand. This carrier showed a red acidic color with methyl red with a pKa of +4.8, but did not show an acidic color with dimethyl yellow with a pKa of +3.3 nor a strong basic color with bromothymol blue with a pKa of +7.1. This showed that the surface of the carrier used in this example, did not have strong acid sites and basic sites and had only weak acid sites with a pKa of +4.8. The amount of thea acid sites with a pKa of +4.8, when titrated with a 0.001N toluene solution of n-butylamine, was 0.6 micromole/g.

EXAMPLES 2-6 AND COMPARATIVE EXAMPLES 1-5

Catalysts were prepared in the same way as in Example 1 except that an alpha-alumina carrier with the silica and sodium contents indicated in Table 1 were used, and the operation was performed so that the amounts of Ag, Na, Ba, Cs and Cl deposited were 12%, 0.2%, 50 ppm, 473 ppm, and 126 ppm.

Using these catalysts, the same reaction as in Example 1 was repeated. Table 1 shows T40, S40, the crush strengths of the carriers, and the results of visual color change reactions in a toluene solution using methyl red with a pKa of +4.8, dimethyl yellow with a pKa of +3.3 and bromothymol blue with a pKa of +7.1.

With regard to Examples 3 and 6 and Comparative Examples 1, 2 and 4, T40 and S40 after reaction for one year are also shown in Table 1. By titration with methyl red with a pKa of +4.8 in toluene, the acid amounts of the carriers used in Examples 2, 3 and 5 were found to be 0.8, 0.8 and 0.6 micromoles/g. The carrier used in Comparative Example 1 which had a very low silica/sodium ratio (=1) showed basicity in a visual color change reaction in toluene with bromothymol blue with a pKa of +7.1. The catalyst obtained by using this catalyst had a selectively 2% lower than that of the catalyst of Example 3 prepared by adding a carrier having an equivalent surface area. After the lapse of 1 year, the difference in selectivity increased to 3%, and the degradation gradient of the selectivity was about 1.5 times that in Example 3. The catalyst of Comparative Example 2 prepared by using a carrier having a sodium content of not more than 0.02% had lower activity and selectivity and crush strength than the catalyst of Example 3 having the same surface area. It is clear that when the carriers having too high a silica/sodium ratio are used as in Comparative Examples 3, 4 and 5, the strengths of the catalyst were very low irrespective of the absolute amount of silica. On the other hand, as shown in Comparative Example 4, the carrier used in this example has strong acidity such that it forms a color with an indicator having a pKa of +3.3. With this catalyst, the reaction temperature is about 1° C. higher than in Example 3, and the selectivity was 1% lower than in Example 3. But one year later, its selectivity was 3% lower than in Example 3. Tus, the degradation gradient of the selectivity was two times, and the active lifetime of the catalyst was much inferior to that of Example 3.

EXAMPLES 7-9 AND COMPARATIVE EXAMPLES 6-8

Catalysts comprising 12% of Ag, 0.2% of Na, 50 ppm of Ba, 630 ppm of Cs and 126 ppm of Cl deposited therein were prepared by the same procedure as in Example 1 using carriers having the silica and sodium contents and the surface areas indicated in Table 2 were used. The results are shown in Table 2. As shown in Comparative Examples 6 to 8, when the silica content is low, the decrease of the selecivity is high. Comparative Example 6 shows that high selectivity cannot be obtained if the carrier has a low Na content.

EXAMPLE 10 AND COMARATIVE EXAMPLE 9

Catalysts comprising 12% of Ag, 50 ppm of Ba, 473 ppm of Cs and 126 ppm of Cl were prepared as in Exasmple 1 using the carriers used in Examples 3 and Comparative Example 3 were used except that sodium was not pre-impregnated and the carriers were not dried. Using these catalysts, the same reaction as in Example 1 was carried out. The results are shown in Table 3.

COMPARATIVE EXAMPLE 10

Using the carrier used in Example 3, a catalyst having a silver loading ratio of 12% but not containing the other components was prepared. The same reaction as in Example 1 was carried out using this catalyst. T40 was 218° C., and S40 was 64%.

TABLE 1

| Run | | $SiO_2$ (wt. %) | Composition of the carrier $SiO_2$ per unit surface area (wt. %/m$^2$) | Na (%) | $SiO_2$/Na | Color reaction of the carrier (*) +4.8 (acidic) | +3.3 (acidic) | +7.1 (basic) | Properties of the carrier Surface area (m$^2$/g) | Average dia-meter ($\mu$) | water absorption (%) | Strength (kg) | Evaluation of the reaction One week later T40 °C. | S40 % | One year later T40 °C. | S40 % |
|---|---|---|---|---|---|---|---|---|---|---|---|---|---|---|---|---|
| Example | 1 | 0.5 | 0.43 | 0.1 | 5 | + | | | 1.16 | 1.5 | 38 | 5.2 | 222 | 80.1 | | |
| | 2 | 1.5 | 1.27 | 0.1 | 15 | ++ | | | 1.18 | 1.5 | 37 | 7.1 | 221 | 80.6 | | |
| | 3 | 3.0 | 2.75 | 0.2 | 15 | ++ | | | 1.09 | 1.6 | 41 | 5.6 | 224 | 80.3 | 234 | 78.4 |
| | 4 | 3.0 | 4.00 | 0.5 | 6 | | | | 0.76 | 2.1 | 33 | 12.1 | 232 | 79.3 | | |
| | 5 | 6.0 | 7.79 | 0.5 | 12 | ++ | | | 0.77 | 2.2 | 33 | 11.3 | 230 | 79.6 | | |
| | 6 | 20.0 | 35.71 | 1.0 | 20 | + | | | 0.65 | 2.7 | 32 | 8.0 | 241 | 79.2 | 254 | 77.0 |
| Comparative Example | 1 | 0.5 | 0.46 | 0.5 | 1 | | | ++ | 1.08 | 1.6 | 36 | 6.7 | 223 | 78.3 | 235 | 75.4 |
| | 2 | 0.5 | 0.45 | 0.02 | 25 | | | + | 1.10 | 1.5 | 40 | 2.5 | 226 | 78.6 | 240 | 75.1 |
| | 3 | 3.0 | 2.65 | 0.05 | 60 | ++ | + | | 1.13 | 1.2 | 37 | 1.1 | 230 | 78.6 | | |
| | 4 | 6.0 | 4.76 | 0.1 | 60 | +++ | + | | 1.26 | 1.7 | 42 | 0.5 | 225 | 79.4 | 240 | 75.4 |
| | 5 | 20.0 | 18.02 | 0.02 | 100 | +++ | + | | 1.11 | 2.0 | 41 | 1.2 | 230 | 78.5 | | |

(*): ++ and +++: very strong; +: strong; no indication: no color reacton took place

TABLE 2

| Run | | Compositions of the carrier | | | | Properties of the carrier | | | Evaluation of the reaction One week later | |
|---|---|---|---|---|---|---|---|---|---|---|
| | | SiO$_2$ (wt. %) | SiO$_2$ per surface area (wt. %/m$^2$) | Na (%) | SiO$_2$/Na | Surface area (m$^2$/g) | Average per diameter ($\mu$) | water absorption (%) | T40 °C. | S40 % |
| Example | 7 | 1.5 | 0.90 | 0.15 | 7 | 1.67 | 1.1 | 37 | 220 | 80.6 |
| | 8 | 3.0 | 1.67 | 0.20 | 15 | 1.80 | 1.5 | 37 | 220 | 81.0 |
| | 9 | 3.0 | 1.00 | 0.20 | 15 | 3.00 | 2.0 | 45 | 215 | 79.8 |
| Comparative | 6 | 0.1 | 0.06 | 0.02 | 5 | 1.80 | 0.9 | 47 | 239 | 77.2 |
| Example | 7 | 0.1 | 0.05 | 0.20 | 0.5 | 1.90 | 0.5 | 30 | 234 | 72.5 |
| | 8 | 0.1 | 0.06 | 1.37 | 0.3 | 1.70 | 0.8 | 37 | 237 | 72.5 |

TABLE 3

| Run | Composition of the carrier | | | | Properties of the carrier | | | Evaluation of the reaction One week later | |
|---|---|---|---|---|---|---|---|---|---|
| | SiO$_2$ (wt. %) | SiO$_2$ per unit surface area (wt. %/m$^2$) | Na (%) | SiO$_2$/Na | Surface area (m$^2$/g) | Average per diameter (u) | water absorption (%) | T40 °C. | S40 % |
| Example 10 | 3.0 | 2.75 | 0.20 | 15 | 1.09 | 1.6 | 41 | 218 | 79.7 |
| Comparative Example 9 | 3.0 | 2.65 | 0.05 | 60 | 1.13 | 1.2 | 37 | 223 | 78.1 |

We claim:

1. A silver-deposited catalyst for the production of ethylene oxide by the oxidation of ethylene, said catalyst comprising
    (1) a carrier composed mainly of alpha-alumina, which carrier does not show acidity in a visual color change method in a toluene solvent using a dimethyl yellow indicator having a pKa of +3.3, and does not show basicity in a color reaction in a toluene solvent using a bromothymol blue having a pKa of +7.1,
    the carrier having a surface area of 0.7 to 3 m$^2$/g, a water absorption of 20 to 50%, an average pore diameter of 0.5 to 3.5 microns, a sodium content of 0.05 to 1% by weight, a silica content of 0.5 to 10% by weight, and a silica/sodium weight ratio of from 3 to 40, and the content of silica per unit surface area of the carrier being 0.1 to 40% by weight/m$^2$, and the carrier having a crush strength of at least 3 kg, and
    (2) as catalyst components, silver and at least one cationic component selected from sodium, potassium, rubidium and cesium.

2. The catalyst of claim 1 in which the cationic component is deposited in the form of an aqueous solution.

3. The catalyst of claim 1 in which the carrier impregnated with silver and/or the cationic component is heat-treated with a superheated system at 130° to 300° C.

* * * * *